(12) United States Patent
Hashimoto et al.

(10) Patent No.: US 11,103,136 B2
(45) Date of Patent: Aug. 31, 2021

(54) PHOTOACOUSTIC MEASUREMENT PROBE AND PROBE UNIT AND PHOTOACOUSTIC MEASUREMENT APPARATUS INCLUDING THE SAME

(71) Applicant: FUJIFILM Corporation, Tokyo (JP)

(72) Inventors: Atsushi Hashimoto, Kanagawa (JP); Kaku Irisawa, Kanagawa (JP); Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 810 days.

(21) Appl. No.: 15/919,515

(22) Filed: Mar. 13, 2018

(65) Prior Publication Data

US 2018/0199820 A1  Jul. 19, 2018

Related U.S. Application Data

(63) Continuation of application No. PCT/JP2016/004110, filed on Sep. 9, 2016.

(30) Foreign Application Priority Data

Sep. 18, 2015  (JP) .............................. JP2015-184762

(51) Int. Cl.
*A61B 5/00* (2006.01)
*A61B 8/00* (2006.01)
*A61B 8/13* (2006.01)

(52) U.S. Cl.
CPC .......... *A61B 5/0095* (2013.01); *A61B 5/0059* (2013.01); *A61B 8/4444* (2013.01);
(Continued)

(58) Field of Classification Search
CPC ... A61B 5/0095; A61B 5/0059; A61B 8/4444; A61B 8/13; A61B 8/4449
See application file for complete search history.

(56) References Cited

U.S. PATENT DOCUMENTS 8,650,960 B2 *  2/2014  Tsujita ................... A61B 8/469
                                                             73/657
2006/0173344 A1  8/2006  Marian et al.
(Continued)

FOREIGN PATENT DOCUMENTS

JP     2008-43440 A    2/2008
JP     2009-261840 A   11/2009
(Continued)

OTHER PUBLICATIONS

Extended European Search Report for European Application No. 16845928.7, dated Jul. 16, 2018.
(Continued)

*Primary Examiner* — Joanne M Hoffman
(74) *Attorney, Agent, or Firm* — Birch, Stewart, Kolasch & Birch, LLP

(57) ABSTRACT

In a photoacoustic measurement probe including an acoustic wave detector and an amplifier for amplifying a detection signal of a photoacoustic wave and a probe unit and a photoacoustic measurement apparatus having such a probe, heat is efficiently dissipated from the probe.

In a probe having an acoustic wave detector and an amplifier, there are provided a first heat conductive member that is in contact with a part of a side plate of a housing and the amplifier to transfer heat generated by the amplifier to the side plate and a second heat conductive member that is in contact with a part different from the part of the side plate and the acoustic wave detector to transfer heat generated by the acoustic wave detector to the side plate.

9 Claims, 12 Drawing Sheets

(52) U.S. Cl.
CPC ............... *A61B 8/546* (2013.01); *A61B 8/13* (2013.01); *A61B 8/4494* (2013.01)

(56) References Cited

U.S. PATENT DOCUMENTS

| | | | |
|---|---|---|---|
| 2013/0303918 A1* | 11/2013 | Miyajima | A61B 8/546 600/459 |
| 2013/0310694 A1* | 11/2013 | Tsujita | A61B 5/0059 600/459 |
| 2013/0331681 A1* | 12/2013 | Tokita | A61B 5/0095 600/407 |
| 2014/0058270 A1* | 2/2014 | Davidsen | G01S 15/8925 600/472 |
| 2014/0251017 A1* | 9/2014 | Kandori | G01N 29/2418 73/661 |
| 2014/0343394 A1* | 11/2014 | Irisawa | A61B 5/0095 600/407 |
| 2015/0126849 A1* | 5/2015 | Kim | G01N 21/1702 600/407 |
| 2015/0182167 A1* | 7/2015 | Kim | A61B 5/6843 600/407 |
| 2017/0231503 A1* | 8/2017 | Nakatsuka | A61B 8/13 600/407 |
| 2018/0146860 A1* | 5/2018 | Abe | A61B 5/0035 |
| 2018/0146861 A1* | 5/2018 | Abe | A61B 5/0095 |

FOREIGN PATENT DOCUMENTS

| | | |
|---|---|---|
| JP | 2012-166009 A | 9/2012 |
| JP | 2012-179350 A | 9/2012 |
| JP | 2013-52023 A | 3/2013 |
| JP | 2014-198234 A | 10/2014 |
| JP | 2014-217529 A | 11/2014 |
| WO | WO 2014/017044 A1 | 1/2014 |

OTHER PUBLICATIONS

International Preliminary Report on Patentability and Written Opinion of the International Searching Authority (Forms PCT/IB/326, PCT/IB/373 and PCT/ISA/237) for Application No. PCT/JP2016/004110, dated Mar. 29, 2018, with an English translation.
International Search Report and English translation (Form PCT/ISA/210) for Application No. PCT/JP2016/004110, dated Dec. 13, 2016.

* cited by examiner

PHOTOACOUSTIC MEASUREMENT PROBE AND PROBE UNIT AND PHOTOACOUSTIC MEASUREMENT APPARATUS INCLUDING THE SAME

CROSS-REFERENCE TO RELATED APPLICATION

This application is a continuation application of International Application No. PCT/JP2016/004110, filed Sep. 9, 2016, the disclosure of which is incorporated herein by reference in its entirety. Further, this application claims priority from Japanese Patent Application No. 2015-184762 filed Sep. 18, 2015, the disclosure of which is incorporated herein by reference in its entirety.

BACKGROUND OF THE INVENTION

1. Field of the Invention

The present invention relates to a photoacoustic measurement probe that emits light toward a subject and absorbs the light to detect photoacoustic waves generated within the subject.

In addition, the present invention relates to a probe unit and a photoacoustic measurement apparatus including such a probe.

2. Description of the Related Art

In recent years, a non-invasive measurement method using a photoacoustic effect has been drawing attention. In the measurement method, a photoacoustic wave, which is an elastic wave generated as a result of emission of pulsed light having an appropriate wavelength (for example, a wavelength band of visible light, near-infrared light, or intermediate infrared light) to a subject and absorption of the energy of the pulsed light by an absorbing substance in the subject, is detected to quantitatively measure the concentration of the absorbing substance. The absorbing substance in the subject is, for example, glucose or hemoglobin contained in blood. In addition, a technique of detecting such a photoacoustic wave and generating a photoacoustic image based on the detection signal is called photoacoustic imaging (PAI) or photoacoustic tomography (PAT).

In photoacoustic imaging, for example, as disclosed in JP2012-166009A and JP2012-179350A, a probe configured to include a light emitting unit for emitting measurement light, such as pulsed light, toward a subject, an acoustic wave detector for detecting an acoustic wave emitted from a part of the subject that has absorbed the measurement light, and a housing in which the light emitting unit and the acoustic wave detector are housed is often used.

In the probe described above, it is required to efficiently dissipate heat generated by the acoustic wave detector and the like so that the temperature of the probe surface in contact with the subject does not become excessively high.

From such a viewpoint, JP2008-043440A discloses a configuration in which, among members for transferring heat generated inside the probe, a member for transferring heat to a probe portion in contact with the inner wall of the lumen of the subject is formed of a material having a relatively low heat conductivity and a member for transferring heat to other probe portions is formed of a relatively high heat conductivity.

SUMMARY OF THE INVENTION

In the probe configured to include the light emitting unit, the acoustic wave detector, and the housing, the detection signal of the photoacoustic wave output from the acoustic wave detector is very weak. Therefore, for example, in the case of acquiring a photoacoustic image, it is desirable to amplify the detection signal of the photoacoustic wave in the probe before amplifying the detection signal of the photoacoustic wave with a receiving circuit or the like outside the probe. In a case where an amplifier is provided in the probe for that purpose, the amplifier becomes a new heat source in addition to the acoustic wave detector. As a result, the temperature of the subject of the probe in contact with the surface tends to be higher.

Since the probe disclosed in JP2008-043440A does not have a configuration for detecting a photoacoustic wave, it is not possible to cope with a further temperature rise in a case where the amplifier is provided as described above.

The present invention has been made in view of the above circumstances, and it is an object of the present invention to obtain an efficient heat dissipation structure capable of preventing the excessive temperature rise of the probe surface in a photoacoustic measurement probe including an acoustic wave detector and an amplifier for amplifying the detection signal of the photoacoustic wave.

In addition, it is an object of the present invention to provide a probe unit and a photoacoustic measurement apparatus for realizing efficient heat dissipation as described above.

There is provided a photoacoustic measurement probe according to the present invention comprising: a light emitting unit that emits measurement light toward a subject; an optical fiber that guides the measurement light to the light emitting unit; an acoustic wave detector that detects an acoustic wave emitted from a part of the subject that has absorbed the measurement light and that includes a plurality of electroacoustic conversion elements arranged in at least a first direction; an amplifier that amplifies an output of the acoustic wave detector; a housing which is a tubular member surrounded by a side plate and in which the light emitting unit, the optical fiber, the acoustic wave detector, and the amplifier are housed; a first heat conductive member that is in contact with a part of the side plate and the amplifier to transfer heat generated by the amplifier to the side plate; and a second heat conductive member that is in contact with a part different from the part of the side plate and the acoustic wave detector to transfer heat generated by the acoustic wave detector to the side plate.

In the photoacoustic measurement probe of the present invention having the configuration described above, it is preferable that the tubular member has a quadrangular tubular shape at least a part of which is surrounded by four side plates, the first heat conductive member is in contact with at least one of two side plates facing each other in the first direction, and the second heat conductive member is in contact with at least one of two side plates different from the two side plates with which the first heat conductive member is in contact.

In such a configuration, in particular, it is preferable that a width of each of the two side plates with which the second heat conductive member is in contact is larger than a width of each of the two side plates with which the first heat conductive member is in contact.

The above-described "quadrangular tubular shape" is not only a tubular shape having a perfect quadrangular cross section but also an approximately quadrangular tubular shape in which a corner portion is rounded or each side plate has a rounded curved surface and an approximately quadrangular tubular shape in which a relatively large quadrangular tubular portion and a relatively small quadrangular tubular portion are connected to each other in the tube axis direction instead of having the same cross-sectional shape over the entire length (length in the tube axis direction) of the tubular member.

In the photoacoustic measurement probe of the present invention, it is preferable that a plurality of the optical fibers extend in a tube axis direction of the tubular member and are arranged to be aligned in a direction parallel to the first direction and the second heat conductive member has a portion disposed around the plurality of optical fibers.

In the photoacoustic measurement probe of the present invention, in a case where the photoacoustic measurement probe further comprising: a fiber fixing member that fixes the plurality of optical fibers to the housing, it is preferable that the second heat conductive member is in contact with the side plate on a proximal end side of the side plate rather than the fiber fixing member.

In the case of considering a structure in which the probe is connected to the light source of the measurement light through the optical fiber, the "proximal end of the side plate" refers to a side plate end on a side where the optical fiber is exposed from the probe toward the light source, that is, a side plate end opposite to the probe surface in contact with the subject during photoacoustic measurement.

In the photoacoustic measurement probe of the present invention, the second heat conductive member may also serve as a fiber fixing member that fixes the plurality of optical fibers to the housing.

In the photoacoustic measurement probe of the present invention, it is preferable that the second heat conductive member is in contact with an inner surface of the side plate through a holding member.

In the photoacoustic measurement probe of the present invention, it is preferable that two light emitting units are provided, the acoustic wave detector is disposed on a distal end side of the tubular member, and on the distal end side of the tubular member, the two light emitting units are disposed with the acoustic wave detector interposed therebetween in a second direction crossing the arrangement direction of a plurality of electroacoustic conversion elements.

The "distal end of the tubular member" is a member distal end on the probe surface side in contact with the subject during photoacoustic measurement.

On the other hand, there is provided a probe unit according to the present invention comprising: the photoacoustic measurement probe according to the present invention described above; a light source that outputs measurement light; and a connection unit that optically connects the measurement light to the light emitting unit of the photoacoustic measurement probe.

There is provided a photoacoustic measurement apparatus according to the present invention comprising: the photoacoustic measurement probe according to the present invention described above; and a signal processing unit that generates a photoacoustic image based on a photoacoustic wave detection signal output from the photoacoustic measurement probe.

The photoacoustic measurement probe of the present invention comprises the first heat conductive member that is in contact with a part of the side plate and the amplifier to transfer the heat generated by the amplifier to the side plate and the second heat conductive member that is in contact with a part different from the part of the side plate and the acoustic wave detector to transfer the heat generated by the acoustic wave detector to the side plate. Therefore, since the heat generated by the amplifier and the heat generated by the acoustic wave detector can be transferred to different portions of the probe side plate to efficiently dissipate heat, it is possible to prevent the excessive temperature rise of the probe surface.

DESCRIPTION OF THE PREFERRED EMBODIMENTS

Hereinafter, embodiments of the present invention will be described in detail with reference to the diagrams.

First Embodiment

Figure 1:
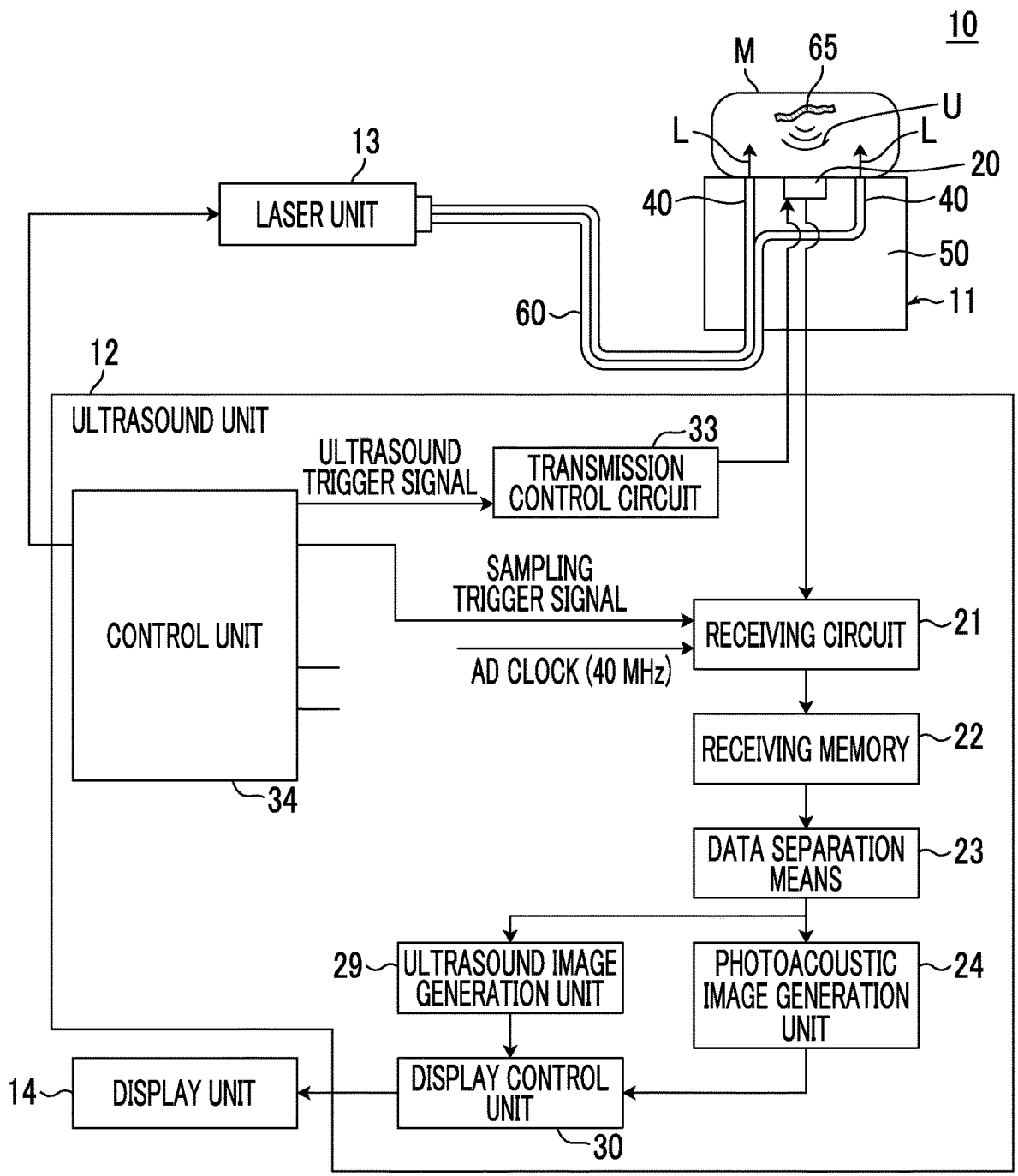
FIG. 1 is a schematic diagram showing the overall configuration of a photoacoustic measurement apparatus according to an embodiment of the present invention.
Figure 2:
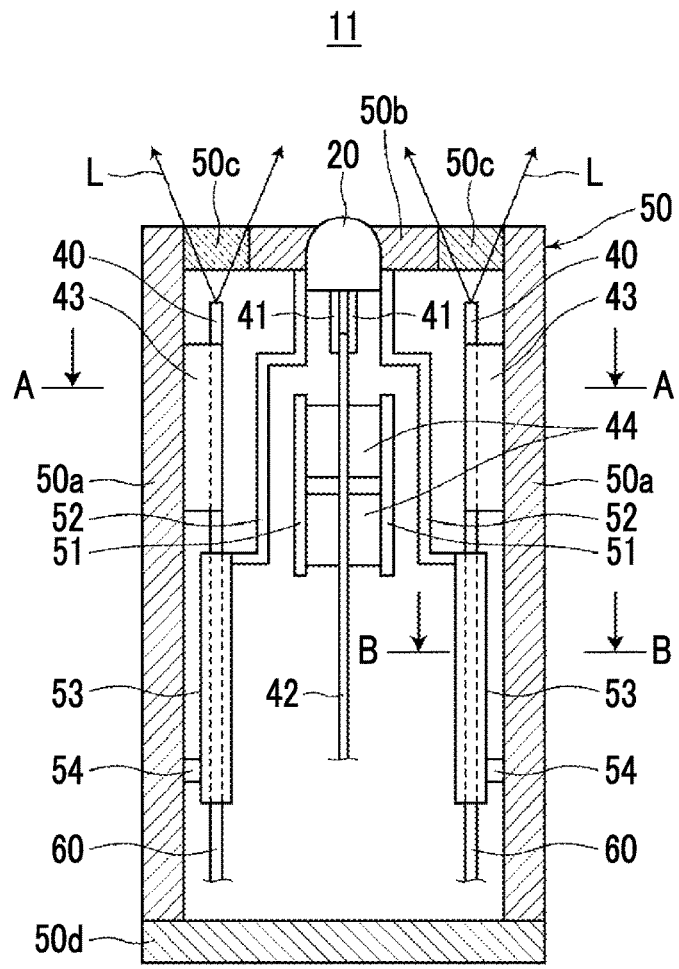
FIG. 2 is a side cross-sectional view showing a probe according to a first embodiment of the present invention.
Figure 3:
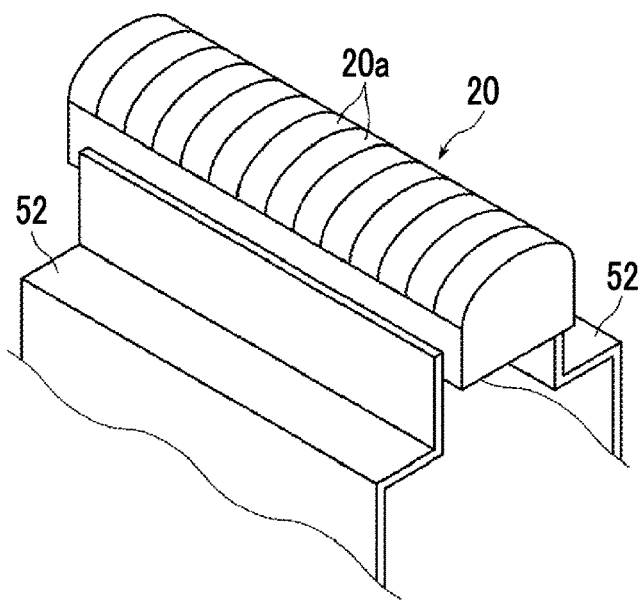
FIG. 3 is a perspective view showing a part of the probe shown in FIG. 2.
Figure 4:
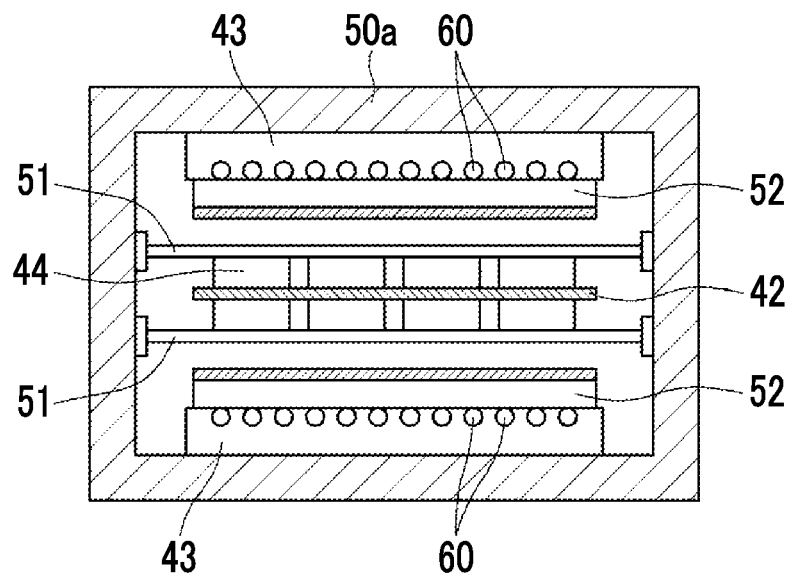
FIG. 4 is a horizontal cross-sectional view showing the cross-sectional shape of a portion taken along the line A-A in FIG. 2.
Figure 5:
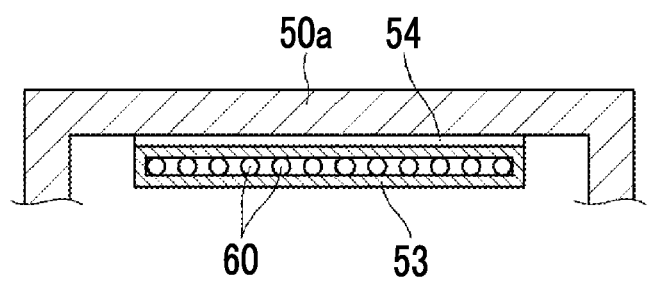
FIG. 5 is a horizontal cross-sectional view showing the cross-sectional shape of a portion taken along the line B-B in FIG. 2.

First, a photoacoustic measurement probe, a probe unit, and a photoacoustic measurement apparatus according to a first embodiment of the present invention will be described. FIG. 1 is a schematic diagram showing the overall configuration of a photoacoustic measurement apparatus 10 of the present embodiment. FIGS. 2 and 3 are a side cross-sectional view and a partial perspective view showing a photoacoustic measurement probe (hereinafter, simply referred to as a probe) 11 used in the photoacoustic measurement apparatus 10, respectively. FIG. 4 is a horizontal cross-sectional view showing a cross section taken along the line A-A in FIG. 2, and FIG. 5 is a horizontal cross-sectional view showing a cross section taken along the line B-B in FIG. 2. In FIG. 1, the shape of the probe 11 is schematically shown.

As an example, the photoacoustic measurement apparatus 10 of the present embodiment has a function of generating a photoacoustic image based on a photoacoustic signal, and includes the probe 11 that is an ultrasound probe, an ultrasound unit 12, a laser unit 13, a display unit 14, and the like as schematically shown in FIG. 1. Hereinafter, these components will be sequentially described.

The probe 11 has, for example, a function of emitting measurement light and an ultrasound wave toward a subject M, which is a living body, and a function of detecting an acoustic wave U propagating through the subject M. That is, the probe 11 can emit (transmit) ultrasound waves to the subject M and detect (receive) reflected ultrasound waves (reflected acoustic waves) that return due to reflection from the subject M. The probe 11 can also detect ultrasound waves (photoacoustic waves) generated within the subject M.

In this specification, the term "acoustic wave" is a term including ultrasound waves and photoacoustic waves. Here, the "ultrasound wave" means an elastic wave transmitted by a probe and its reflected wave, and the "photoacoustic wave" means an elastic wave generated due to an absorber 65 absorbing measurement light. The acoustic wave emitted from the probe 11 is not limited to the ultrasound wave, and an acoustic wave having an audible frequency may be used as long as an appropriate frequency can be selected according to an examination target, measurement conditions, or the like. As the absorber 65 in the subject M, for example, blood vessels, a metal member, and the like can be mentioned.

Generally, the probe 11 corresponding to sector scanning, the probe 11 corresponding to linear scanning, the probe 11 corresponding to convex scanning, and the like are prepared. Among these, an appropriate one selected according to an imaging part is used. An optical fiber 60 as a connection unit for guiding laser light L, which is measurement light emitted from the laser unit 13 to be described later, to the light emitting unit 40 is connected to the probe 11.

As shown in detail in FIG. 2, the probe 11 includes a transducer array 20 that is an acoustic wave detector, a total of two light emitting units 40 disposed on both sides of the transducer array 20 with the transducer array 20 interposed therebetween, and a housing 50 in which the transducer array 20 and the two light emitting units 40 are housed.

As shown in FIG. 2, the housing 50 is configured to include, for example, a tubular member surrounded by four side plates 50a and a top plate 50b and a bottom plate 50d that close both ends of the tubular member. The side plate 50a, the top plate 50b, and the bottom plate 50d are formed of synthetic resin, such as acrylonitrile butadiene styrene (ABS) resin, as an example. A transparent window 50c formed of, for example, synthetic resin or glass that transmits the laser light L emitted from the light emitting unit 40 is fitted in the top plate 50b. The side plate 50a, the top plate 50b, and the bottom plate 50d may be integrally molded, or may be bonded to each other after being formed as separate members.

In the present embodiment, the transducer array 20 also functions as an ultrasound wave transmission element. The transducer array 20 is connected to a preamplifier 44 to be described later, a circuit for ultrasound wave transmission, a circuit for acoustic wave reception, and the like through a terminal 41 and a wiring 42.

As shown in FIG. 3, the transducer array 20 includes a plurality of ultrasound transducers 20a as electroacoustic conversion elements that are aligned in one direction. The alignment direction of the ultrasound transducers 20a is referred to as a "first direction". The first direction is a direction perpendicular to the plane of paper in FIG. 2, and is a horizontal direction in FIG. 4. The ultrasound transducer 20a is, for example, a piezoelectric element formed of a polymer film, such as piezoelectric ceramics or polyvinylidene fluoride (PVDF). The ultrasound transducer 20a has a function of converting the received acoustic wave U into an electrical signal. The transducer array 20 may include an acoustic lens.

In the present embodiment, as described above, the transducer array 20 has a plurality of ultrasound transducers 20a arranged in a one-dimensional manner. However, a transducer array in which a plurality of ultrasound transducers 20a are arranged in a two-dimensional manner may be used.

The ultrasound transducer 20a also has a function of transmitting ultrasound waves. That is, in a case where an alternating voltage is applied to the ultrasound transducer 20a, the ultrasound transducer 20a generates an ultrasound wave having a frequency corresponding to the frequency of the alternating voltage. Transmission and reception of ultrasound waves may be separated from each other. That is, for example, ultrasound waves may be transmitted from a position different from the probe 11, and reflected ultrasound waves of the transmitted ultrasound waves may be received by the probe 11.

The light emitting unit 40 is a unit that emits the laser light L guided by the optical fiber 60 toward the subject M. In the present embodiment, the light emitting unit 40 is formed by using a distal end portion of the optical fiber 60, that is, an end portion far from the laser unit 13 that is a light source of measurement light. As shown in FIGS. 1 and 2, in the present embodiment, the two light emitting units 40 are disposed on both sides of the transducer array 20, for example, in the elevation direction with the transducer array 20 interposed therebetween. In a case where a plurality of ultrasound transducers 20a are arranged in a one-dimensional manner, the elevation direction is a direction perpendicular to the arrangement direction (first direction described above) and parallel to the detection surface of the transducer array 20. The elevation direction is referred to as a "second direction". The second direction is a horizontal direction in FIG. 2, and is a vertical direction in FIG. 4.

As shown in FIG. 2, a portion close to the distal end of the optical fiber 60 is fixed to the inner surface of the side plate 50a of the housing 50 by a fiber fixing member 43. In the fiber fixing member 43, grooves into which one optical fiber 60 or a plurality of optical fibers 60 are fitted so as to be fixed are formed on one surface (surface facing the wiring 42 side in FIG. 2) side of a rectangular parallelepiped member formed of, for example, synthetic resin.

The light emitting unit may be formed by using a light guide plate and a diffusion plate that are optically coupled to the distal end of the optical fiber 60. Such a light guide plate can be formed by using, for example, an acrylic plate or a quartz plate. As the diffusion plate, it is possible to use a lens diffusion plate in which microlenses are randomly arranged on a substrate, a quartz plate in which, for example, diffusing fine particles are dispersed, or the like. As the lens diffusion plate, a holographic diffusion plate or an engineering diffusion plate may be used.

The laser unit 13 shown in FIG. 1 has, for example, a flash lamp excitation Q-switch solid state laser, such as a Q-switch alexandrite laser, and emits the laser light L as measurement light. The laser unit 13 is configured to receive a trigger signal from a control unit 34 of the ultrasound unit 12 and output the laser light L, for example. It is preferable that the laser unit 13 outputs the pulsed laser light L having a pulse width of 1 to 100 nsec (nanoseconds).

The wavelength of the laser light L is appropriately selected according to the light absorption characteristics of the absorber 65 in the subject M that is a measurement target. For example, in a case where the measurement target is hemoglobin in the living body, that is, in the case of imaging blood vessels, it is generally preferable that the wavelength is a wavelength belonging to the near-infrared wavelength range. The near-infrared wavelength range means a wavelength range of approximately 700 to 850 nm. However, it is natural that the wavelength of the laser light L is not limited thereto. In addition, the laser light L may have a single wavelength, or may include a plurality of wavelengths of, for example, 750 nm and 800 nm. In a case where the laser light L includes a plurality of wavelengths, light beams having these wavelengths may be simultaneously emitted, or may be emitted while being switched alternately.

In addition to the alexandrite laser described above, the laser unit 13 can be formed by using a YAG-second harmonic generation (SHG)-optical parametric oscillation (OPO) laser, a Ti-Sapphire (titanium sapphire) laser, or the like capable of outputting laser light in the near-infrared wavelength range similarly.

The laser unit 13 as a light source forms a probe unit together with the probe 11 and the optical fiber 60.

The optical fiber 60 guides the laser light L emitted from the laser unit 13 to the two light emitting units 40. The optical fiber 60 is not particularly limited, and known fibers, such as a quartz fiber, can be used. For example, one thick optical fiber may be used, or a bundle fiber in which a plurality of optical fibers are bundled may be used. As an example, in a case where a bundle fiber is used, the bundle fiber is arranged so that the laser light L is incident from the light incidence end surface of a group of fiber portions, and distal end portions of two branched fiber portions of the bundle fiber form the light emitting unit 40 as described above.

The ultrasound unit 12 has a receiving circuit 21, a receiving memory 22, a data separation unit 23, a photoacoustic image generation unit 24, an ultrasound image generation unit 29, a display control unit 30, a transmission control circuit 33, and the control unit 34.

The control unit 34 controls each unit of the photoacoustic measurement apparatus 10, and includes a trigger control circuit (not shown) in the present embodiment. The trigger control circuit transmits an optical trigger signal to the laser unit 13, for example, in the case of acquiring a photoacoustic image. As a result, the flash lamp of the excitation source is turned on in the Q-switch solid state laser of the laser unit 13, and excitation of the laser rod is started. While the excitation state of the laser rod is maintained, the laser unit 13 is ready to output the laser light L.

Thereafter, the control unit 34 transmits a Q-switch trigger signal to the laser unit 13 from the trigger control circuit. That is, the control unit 34 controls the output timing of the laser light L from the laser unit 13 using the Q-switch trigger signal. The control unit 34 transmits a sampling trigger signal to the receiving circuit 21 simultaneously with the transmission of the Q-switch trigger signal. This sampling trigger signal specifies the sampling start timing of the photoacoustic signal in an analog to digital convertor (AD converter) of the receiving circuit 21. Thus, it is possible to sample a photoacoustic signal in synchronization with the output of the laser light L by using the sampling trigger signal.

In the case of acquiring an ultrasound image, the control unit 34 transmits an ultrasound wave transmission trigger signal for giving an instruction to transmit ultrasound waves to the transmission control circuit 33. In a case where the ultrasound wave transmission trigger signal is received, the transmission control circuit 33 makes the probe 11 transmit ultrasound waves. The control unit 34 transmits a sampling trigger signal to the receiving circuit 21 according to the timing of ultrasound wave transmission, thereby starting the sampling of a reflected ultrasound signal.

In the case of acquiring the photoacoustic image or the ultrasound image described above, the position of the probe 11 is gradually changed in the above-described elevation direction with respect to the subject M, and the subject M is scanned with the laser light L or ultrasound waves. Therefore, sampling of the photoacoustic signal or the reflected ultrasound signal is performed while shifting the acoustic wave detection line line by line in synchronization with the scanning. The scanning may be performed by manually moving the probe 11 by the operator or may be performed using an automatic scanning mechanism.

The receiving circuit 21 receives a detection signal output from the transducer array 20 of the probe 11, and stores the received detection signal in the receiving memory 22. Typically, the receiving circuit 21 is configured to include a low noise amplifier, a variable gain amplifier, a low pass filter, and an AD converter. The detection signal of the probe 11 is amplified by the low noise amplifier, and then gain adjustment according to the depth is performed by the variable gain amplifier and a high-frequency component is cut by the low pass filter. Then, conversion into a digital signal is performed by the AD converter, and the digital signal is stored in the receiving memory 22. The receiving circuit 21 is formed by using one IC, for example.

In the present embodiment, the probe 11 outputs a detection signal of photoacoustic waves and a detection signal of reflected ultrasound waves. Therefore, digitized detection signals (sampling data) of photoacoustic waves and reflected ultrasound waves are stored in the receiving memory 22. The data separation unit 23 reads the sampling data (photoacoustic data) of the photoacoustic wave detection signal from the receiving memory 22, and transmits the sampling data to the photoacoustic image generation unit 24. The data separation unit 23 reads the sampling data (reflected ultrasound data) of the reflected ultrasound detection signal from the receiving memory 22, and transmits the sampling data to the ultrasound image generation unit 29.

The photoacoustic image generation unit 24 reconstructs data of one line by adding up the pieces of photoacoustic data stored in the receiving memory 22 with a delay time corresponding to the position of the transducer array 20 of the probe 11, and generates data of a tomographic image (photoacoustic image) based on the photoacoustic data of each line. The photoacoustic image generation unit 24 may perform reconstruction using a circular back projection (CBP) instead of the delay addition method. Alternatively, the photoacoustic image generation unit 24 may perform reconstruction using a Hough transform method or a Fourier transform method. The photoacoustic image generation unit 24 outputs the data of the photoacoustic image generated as described above to the display control unit 30.

As is apparent from the above description, the photoacoustic image generation unit 24 forms a signal processing unit in the photoacoustic measurement apparatus of the present invention.

The ultrasound image generation unit 29 generates data of a tomographic image (ultrasound image) by performing basically the same processing as for the photoacoustic data on the reflected ultrasound data stored in the receiving memory 22. The ultrasound image generation unit 29 outputs the data of the ultrasound image generated as described above to the display control unit 30.

The display control unit 30 displays a photoacoustic image on the display unit 14 based on the data of the photoacoustic image, and displays an ultrasound image on the display unit 14 based on the data of the ultrasound image. These two images are separately displayed on the display unit 14, or are combined to be displayed on the display unit 14 as a composite image. In the latter case, the display control unit 30 performs image combination by superimposing the photoacoustic image and the ultrasound image, for example. In this manner, in a case where the ultrasound image is generated and displayed in addition to the photoacoustic image, a portion that cannot be imaged in the photoacoustic image can be observed in the ultrasound image.

Next, in the photoacoustic measurement apparatus 10 having the basic constitution as described above, a configuration for efficiently dissipating heat generated by the probe 11 will be described. Unless otherwise stated, the directions of up, down, left, and right in the probe 11 described below refer to directions in a state in which the probe 11 is disposed as shown in FIG. 2.

The detection signal output from the transducer array 20 of the probe 11 is input to the receiving circuit 21 shown in FIG. 1 as described above. However, since the detection signal of the photoacoustic wave is weaker than the detection signal of the reflected ultrasound wave, it is desirable to amplify the detection signal of the photoacoustic wave at the stage before the receiving circuit 21. In the present embodiment, therefore, as shown in FIG. 2, the preamplifier 44 is provided in the housing 50. The preamplifier 44 is connected to the transducer array 20 and the receiving circuit 21 through the wiring 42. The preamplifier 44 is formed by using one integrated circuit (IC), for example. In this case, the IC may be configured to include a circuit other than the preamplifier 44.

Originally, in the probe 11, the heat generated by the transducer array 20 is easily transferred to the subject M directly or through the top plate 50*b*. In a case where the preamplifier 44 as a new heat source is provided in addition to the transducer array 20, there is a possibility that the transducer array 20 and the top plate 50*b* in contact with the subject M will be further heated. Therefore, it is necessary to suppress a temperature rise in the transducer array 20 and the top plate 50*b*. For this purpose, suppressing the heat generation itself of the preamplifier 44 may be considered. In such a case, however, problems relevant to the degree of satisfaction or the display image quality of the photoacoustic measurement apparatus 10, such as a reduction in a value applied to the transducer array 20 in order to transmit ultrasound waves or a reduction in the sampling rate of the detection signal in the receiving circuit 21, occur.

Therefore, in the present embodiment, the aforementioned problem can be prevented by efficiently dissipating the heat generated from the transducer array 20 and the preamplifier 44. Hereinafter, the configuration for the purpose will be described in detail. A heat transfer plate 51 as a first heat conductive member formed of a high heat conductivity material is tightly fixed to both the left and right sides of the preamplifier 44. One end and the other end of each heat transfer plate 51 are tightly fixed to the inner surfaces of the two side plates 50*a* facing each other of the housing 50. The two side plates 50*a* are the left and right side plates 50*a* in FIG. 4, that is, the side plates 50*a* facing each other in the first direction described above.

Here, the above "high heat conductivity material" generally refers to a material having a heat conductivity of 1 W/m·K or more. As specific examples of such a high heat conductivity material, it is possible to apply pyrolytic graphite, such as aluminum, stainless steel, and "PGS graphite sheet" manufactured by Panasonic Electronic Devices Co., Ltd., and high heat conductivity resin represented by "3M (registered trademark) hyper soft heat dissipation material" manufactured by 3M Company. One end and the other end of the heat transfer plate 51 are each processed into a T shape, and the fixing strength with respect to the side plate 50*a* is enhanced. This fixing is realized, for example by bonding using an adhesive with heat resistance or by bonding using screwing.

On the other hand, an upper end portion of a heat transfer plate 52 formed of a high heat conductivity material is fixed to each of the left and right sides of the lower portion of the transducer array 20. The heat transfer plate 52 can be formed of the same high heat conductivity material as that used for the heat transfer plate 51 exemplified above. As shown in the diagram, the heat transfer plate 52 is formed in a plate shape bent at three places, and the lower end of each heat transfer plate 52 is fixed to the upper portion of the heat transfer member 53.

As shown in FIG. 5, one heat transfer member 53 has an approximately thin quadrangular tubular shape having a portion disposed around a plurality of optical fibers 60 arranged in a column, and is formed of a high heat conductivity material. As the high heat conductivity material, for example, a metal foil, such as a copper foil or an aluminum foil, can be applied.

One end of a heat transfer plate 54 is fixed to a portion close to the lower end of the heat transfer member 53. The other ends of the two heat transfer plates 54 are tightly fixed to the inner surfaces of the two side plates 50*a* facing each other of the housing 50. That is, the heat transfer member 53 is fixed to the side plate 50*a* through the heat transfer plate 54 on the proximal end side (side opposite to the surface of the probe 11) of the side plate 50*a* rather than the fiber fixing member 43. The two side plates 50*a* are the upper and lower side plates 50*a* in FIG. 4, that is, the side plates 50*a* facing each other in the second direction described above. The heat transfer plate 54 can also be formed of the same high heat conductivity material as that used for the heat transfer plate 51 exemplified above.

The heat transfer plate 52, the heat transfer member 53, and the heat transfer plate 54 described above form a second heat conductive member in the present invention. The heat transfer member 53 also has a function of protecting a plurality of optical fibers 60. In particular, in a case where the heat transfer member 53 is a highly elastic member, it is possible to prevent the optical fiber 60 from being damaged by vibration externally applied to the probe 11 or to prevent positional deviation.

The widths of the heat transfer plate 52 and the heat transfer plate 54 are almost the same as the width of the heat transfer member 53 surrounding a plurality of optical fibers 60. The heat transfer plate 52 is fixed to the transducer array 20 and the heat transfer plate 54 is fixed to the housing side plate 50*a*, for example, by bonding using an adhesive with heat resistance or by bonding using screwing. On the other hand, the heat transfer plate 52 and the heat transfer plate 54 are fixed to the heat transfer member 53, for example, by bonding using an adhesive with heat resistance.

In the configuration described above, heat generated mainly from the preamplifier 44 is satisfactorily transferred to the two side plates 50*a* through the heat transfer plate 51. In addition, heat generated mainly from the transducer array 20 is satisfactorily transferred to the two side plates 50*a* through the heat transfer plate 52, the heat transfer member 53, and the heat transfer plate 54. Since the total area of the four side plates 50a is considerably larger than the area of the top plate 50b of the housing 50, heat can be satisfactorily dissipated from the side plates 50a. As a result, an excessive increase in the temperature of the top plate 50b of the housing 50 in contact with the subject M or the transducer array 20 and an excessive increase in the temperature of the vicinity thereof are prevented.

Heat generated mainly from the preamplifier 44 may be transferred to one side plate 50a through the heat transfer plate 51. In addition, heat generated mainly from the transducer array 20 may be transferred to one side plate 50a through the heat transfer plate 52, the heat transfer member 53, and the heat transfer plate 54.

The heat conductivity of the high heat conductivity materials listed above is usually about two to three orders (in the case of metal) and one to two orders (in the case of high heat conductivity resin) higher than the heat conductivity of ordinary resins, such as ABS resin that is often used as the material of the housing 50. Therefore, compared with a case where the housing itself is used as the heat transfer path, heat generated near the surface of the probe 11 (the surface of the top plate 50b or the surface of the transducer array 20) can be efficiently transferred to the base side of the probe 11, that is, a side far from the probe surface.

In the present embodiment, the heat generated mainly from the transducer array 20 is transferred to the side plate 50a through the heat transfer member 53 having the above-described shape. Therefore, in a case where the above-described second direction (elevation direction) is considered, even if a plurality of optical fibers 60 are present between the transducer array 20 and the side plate 50a, the above heat transfer can be realized.

In the present embodiment, the heat generated mainly from the preamplifier 44 is transferred in the above-described first direction, that is, in the array direction of the ultrasound transducer 20a in the transducer array 20, and the heat generated mainly from the transducer array 20 is transferred in the above-described second direction (elevation direction). However, on the contrary, the heat generated mainly from the preamplifier 44 may be transferred in the second direction (elevation direction), and the heat generated mainly from the transducer array 20 may be transferred in the first direction (array direction). The above points also apply to second to fourth embodiments to be described later.

However, as shown in FIG. 4, the two side plates 50a facing each other in the second direction (elevation direction) among the four side plates 50a of the housing 50 generally have larger widths than the two side plates 50a facing each other in the first direction (array direction) since it is necessary for the transducer array 20 to have a sufficient length to some extent. In addition, the amount of heat generated by the transducer array 20 is usually larger than the amount of heat generated by the preamplifier 44. Therefore, it can be said that it is more efficient in terms of heat dissipation that the heat generated mainly from the transducer array 20 is transferred in the second direction (elevation direction) so as to be dissipated from the two wider side plates 50a facing each other in the second direction.

Second Embodiment

Figure 6:
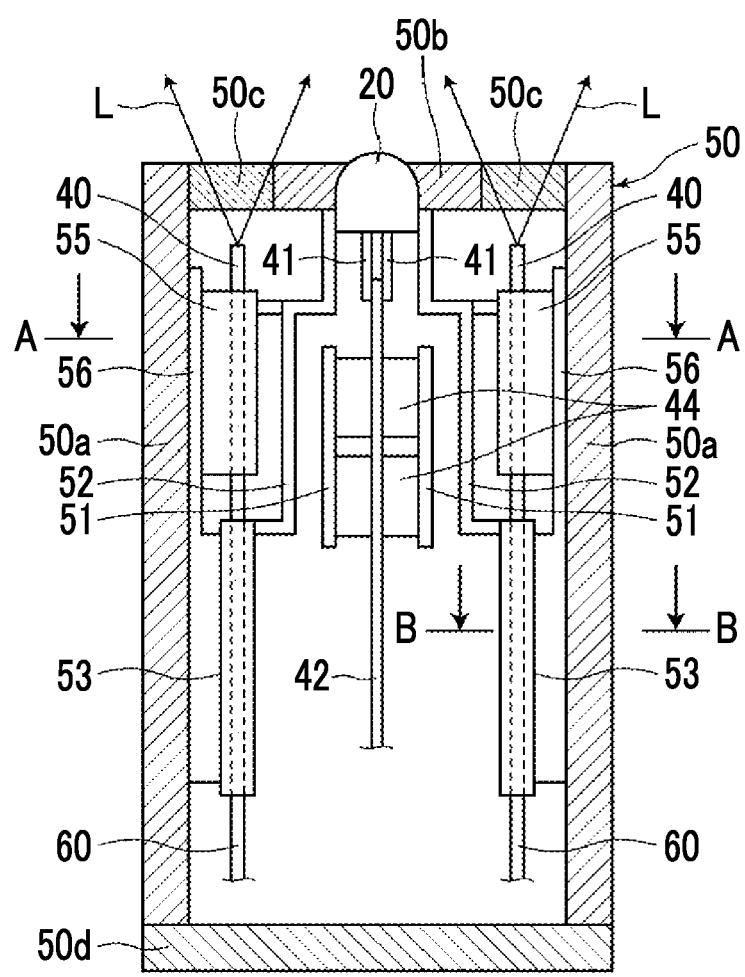
FIG. 6 is a side cross-sectional view showing a probe according to a second embodiment of the present invention.

Next, a probe 211 according to a second embodiment of the present invention will be described with reference to FIG. 6. FIG. 6 shows the side cross-sectional shape of the probe 211 of the present embodiment. In FIG. 6, the same elements as in FIG. 2 described previously are denoted by the same reference numerals, and the explanation thereof will be omitted unless particularly required (the same hereinbelow). The probe 211 is different from the probe 11 shown in FIG. 2 in terms of the configuration of the second heat conductive member. That is, in the present embodiment, instead of the fiber fixing member 43 shown in FIG. 2, a fiber fixing member 55 formed of a high heat conductivity material is applied. As specific examples of such a high heat conductivity material, it is possible to apply pyrolytic graphite, such as aluminum, stainless steel, and "PGS graphite sheet" manufactured by Panasonic Electronic Devices Co., Ltd., high heat conductivity resin represented by "3M (registered trademark) hyper soft heat dissipation material" manufactured by 3M Company, and a material in which a high heat conductivity material, such as a copper foil, is disposed on the surface of such a high heat conductivity resin. In the fiber fixing member 55, grooves into which one optical fiber 60 or a plurality of optical fibers 60 are fitted so as to be fixed are formed on the slightly inner side from one surface (surface facing the wiring 42 side in FIG. 6) of a rectangular parallelepiped member.

The heat transfer plate 52 is tightly fixed to the heat transfer member 53 and is also tightly fixed to the fiber fixing member 55. The heat transfer member 53 and the fiber fixing member 55 are tightly fixed to a frame member 56 as a holding member, and the frame member 56 is tightly fixed to the inner surface of the side plate 50a of the housing 50. That is, the heat transfer member 53 and the fiber fixing member 55 are fixed to the inner surface of the side plate 50a with the frame member 56 interposed therebetween. In this manner, a portion close to the distal end of the optical fiber 60 is fixed to the inner surface of the side plate 50a of the housing 50 by the fiber fixing member 55. The frame member 56 can also be formed of the same high heat conductivity material as that used for the heat transfer plate 51 exemplified above.

The heat transfer plate 52, the heat transfer member 53, the fiber fixing member 55, and the frame member 56 described above form a second heat conductive member in the present invention. On the other hand, the first heat conductive member is formed by using the heat transfer plate 51 in the same manner as in the configuration shown in FIG. 2.

In the configuration described above, heat generated mainly from the preamplifier 44 is satisfactorily transferred to the two side plates 50a through the heat transfer plate 51. In addition, heat generated mainly from the transducer array 20 is satisfactorily transferred to the two side plates 50a through the heat transfer plate 52, the fiber fixing member 55, and the frame member 56 and through the heat transfer plate 52, the heat transfer member 53, and the frame member 56. Therefore, heat can be satisfactorily dissipated from the four side plates 50a. As a result, also in the present embodiment, an excessive increase in the temperature of the top plate 50b of the housing 50 in contact with the subject M or the transducer array 20 and an excessive increase in the temperature of the vicinity thereof are prevented.

In particular, in the present embodiment, by applying the fiber fixing member 55 and the frame member 56 that are formed of a high heat conductivity material, the area of the second heat conductive member in contact with the side plate 50a of the housing 50 can be further increased compared to the first embodiment. As a result, in the probe 211 of the present embodiment, the heat dissipation effect is particularly high.

Third Embodiment

Next, a probe 311 according to a third embodiment of the present invention will be described with reference to FIG. 7.

Figure 7:
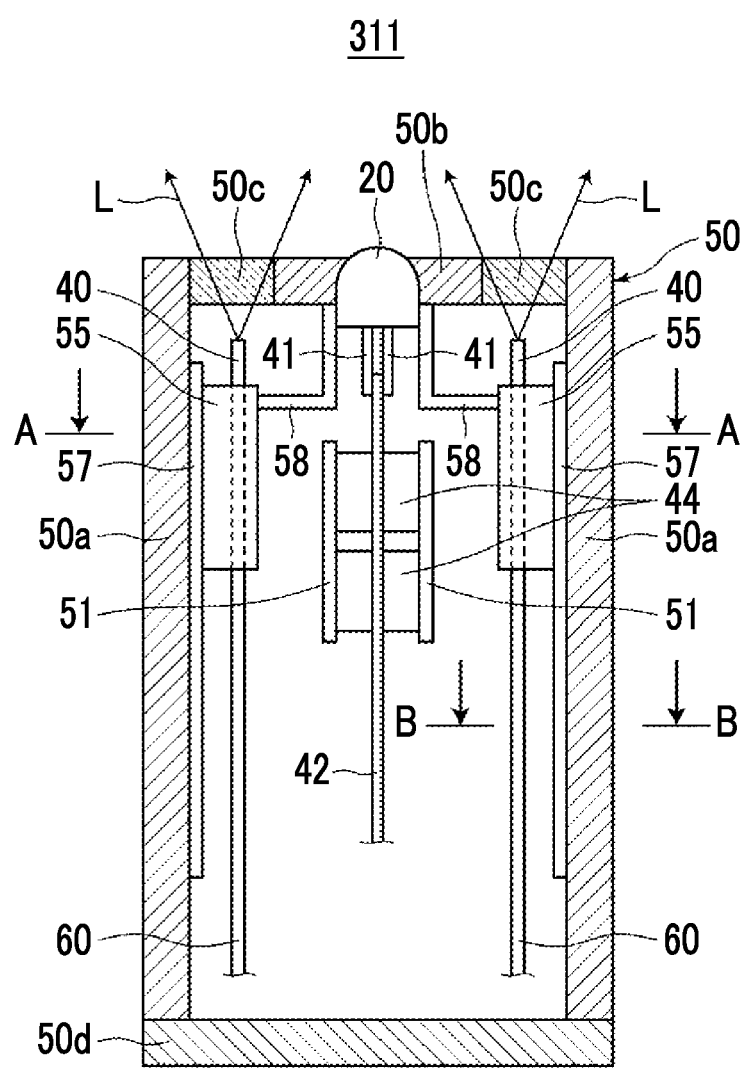
FIG. 7 is a side cross-sectional view showing a probe according to a third embodiment of the present invention.

FIG. 7 shows the side cross-sectional shape of the probe 311 of the present embodiment. The probe 311 is basically different from the probe 211 shown in FIG. 6 in that a heat transfer plate 58 having one end portion and the other end portion tightly fixed to the transducer array 20 and the fiber fixing member 55, respectively, is used instead of the heat transfer plate 52 and the heat transfer member 53 is omitted. Since the heat transfer member 53 is omitted, a simple plate-shaped frame member 57 is used, which is somewhat different from the frame member 56 in the configuration shown in FIG. 6.

In the configuration described above, heat generated mainly from the preamplifier 44 is satisfactorily transferred to the two side plates 50a through the heat transfer plate 51. In addition, heat generated mainly from the transducer array 20 is satisfactorily transferred to the two side plates 50a through the heat transfer plate 58, the fiber fixing member 55, and the frame member 57. Therefore, heat can be satisfactorily dissipated from the four side plates 50a. As a result, also in the present embodiment, an excessive increase in the temperature of the top plate 50b of the housing 50 in contact with the subject M or the transducer array 20 and an excessive increase in the temperature of the vicinity thereof are prevented.

Fourth Embodiment

Figure 8:
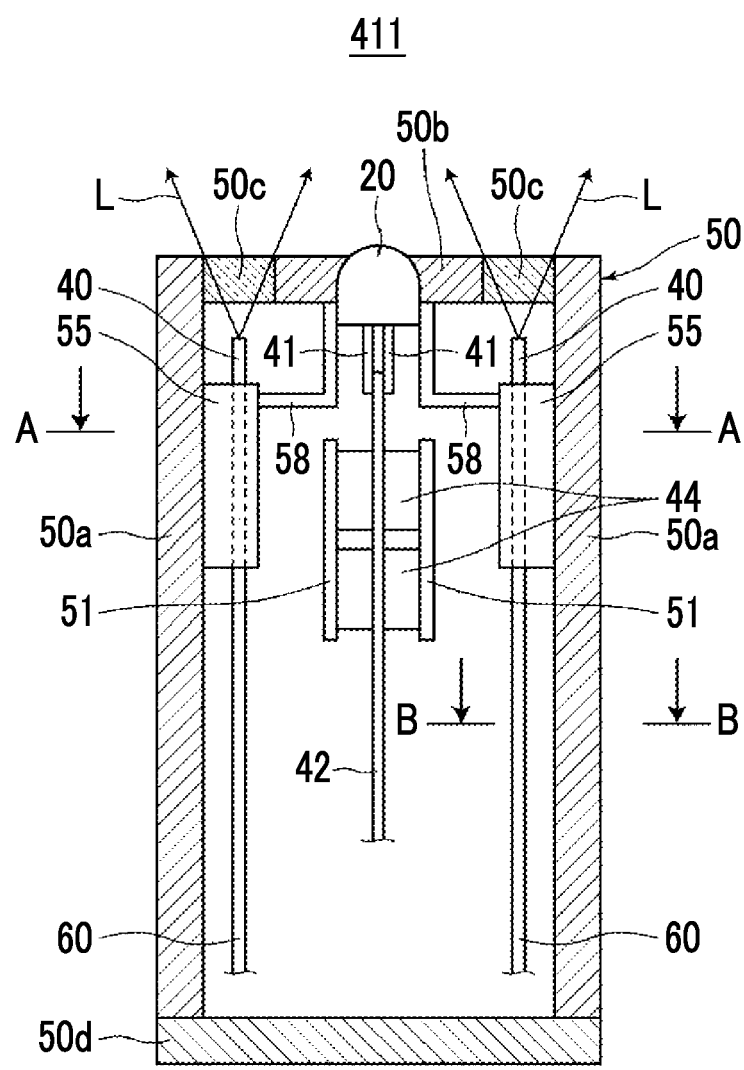
FIG. 8 is a side cross-sectional view showing a probe according to a fourth embodiment of the present invention.

Next, a probe 411 according to a fourth embodiment of the present invention will be described with reference to FIG. 8. FIG. 8 shows the side cross-sectional shape of the probe 411 of the present embodiment. The probe 411 is basically different from the probe 311 shown in FIG. 7 in that the frame member 57 is omitted. That is, the fiber fixing member 55 is tightly fixed directly to the inner surface of the side plate 50a of the housing 50.

In the configuration described above, heat generated mainly from the preamplifier 44 is satisfactorily transferred to the two side plates 50a through the heat transfer plate 51. In addition, heat generated mainly from the transducer array 20 is satisfactorily transferred to the two side plates 50a through the heat transfer plate 58 and the fiber fixing member 55. Therefore, heat can be satisfactorily dissipated from the four side plates 50a. As a result, also in the present embodiment, an excessive increase in the temperature of the top plate 50b of the housing 50 in contact with the subject M or the transducer array 20 and an excessive increase in the temperature of the vicinity thereof are prevented.

Compared with the probe 411 of the present embodiment, in the probe 311 shown in FIG. 7, the frame member 57 that extends largely up to the base side of the probe is used. Therefore, since the area of the second heat conductive member in contact with the side plate 50a of the housing 50 is larger than that in the probe 411 of the present embodiment by the amount of extension, the heat dissipation effect is high.

Fifth Embodiment

Figure 9:
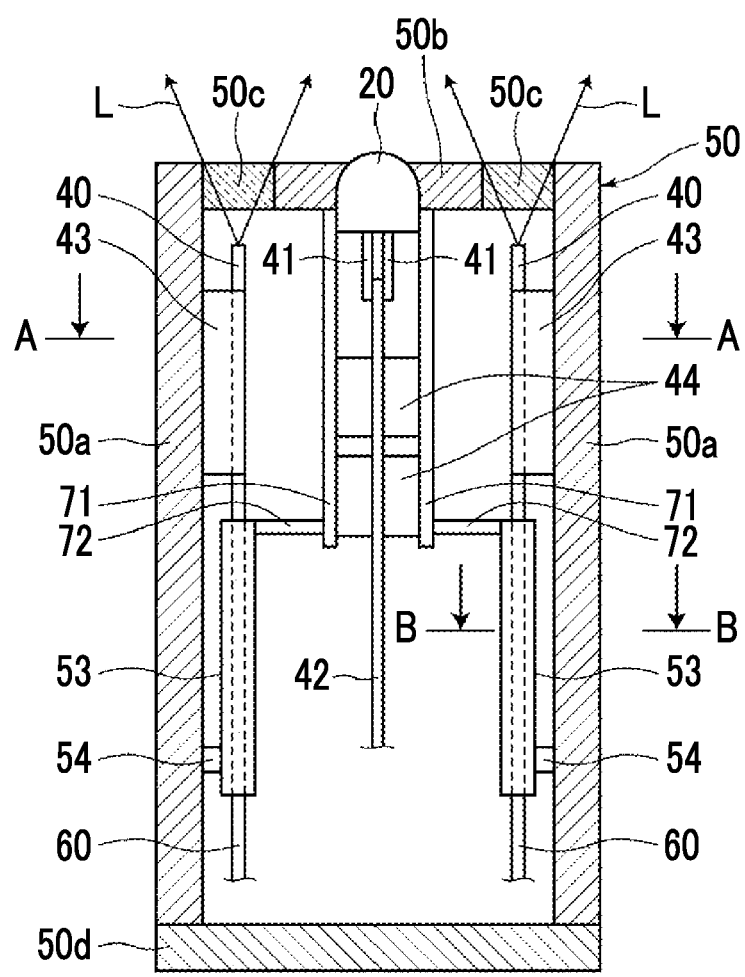
FIG. 9 is a side cross-sectional view showing a probe according to a fifth embodiment of the present invention.

Next, a probe 511 according to a fifth embodiment of the present invention will be described with reference to FIG. 9. FIG. 9 shows the side cross-sectional shape of the probe 511 of the present embodiment. The probe 511 is different from the probe 11 of the first embodiment shown in FIG. 2 in that a heat transfer plate 71 tightly fixed to the transducer array 20 and the preamplifier 44 and a heat transfer plate 72 having one end and the other end tightly fixed to the heat transfer plate 71 and the heat transfer member 53, respectively, are used instead of the heat transfer plate 51 and the heat transfer plate 52.

In the configuration described above, heat generated mainly from the preamplifier 44 and heat generated mainly from the transducer array 20 are satisfactorily transferred to the two side plates 50a through the heat transfer plate 71, the heat transfer plate 72, the heat transfer member 53, and the heat transfer plate 54. Therefore, heat can be satisfactorily dissipated from the two side plates 50a. As a result, also in the present embodiment, an excessive increase in the temperature of the top plate 50b of the housing 50 in contact with the subject M or the transducer array 20 and an excessive increase in the temperature of the vicinity thereof are prevented.

In the present embodiment, the heat generated mainly from the preamplifier 44 and the transducer array 20 is transferred in the above-described second direction (elevation direction). However, on the contrary, heat may be transferred in the above-described first direction (array direction). The above points also apply to sixth to eighth embodiments to be described later.

Sixth Embodiment

Figure 10:
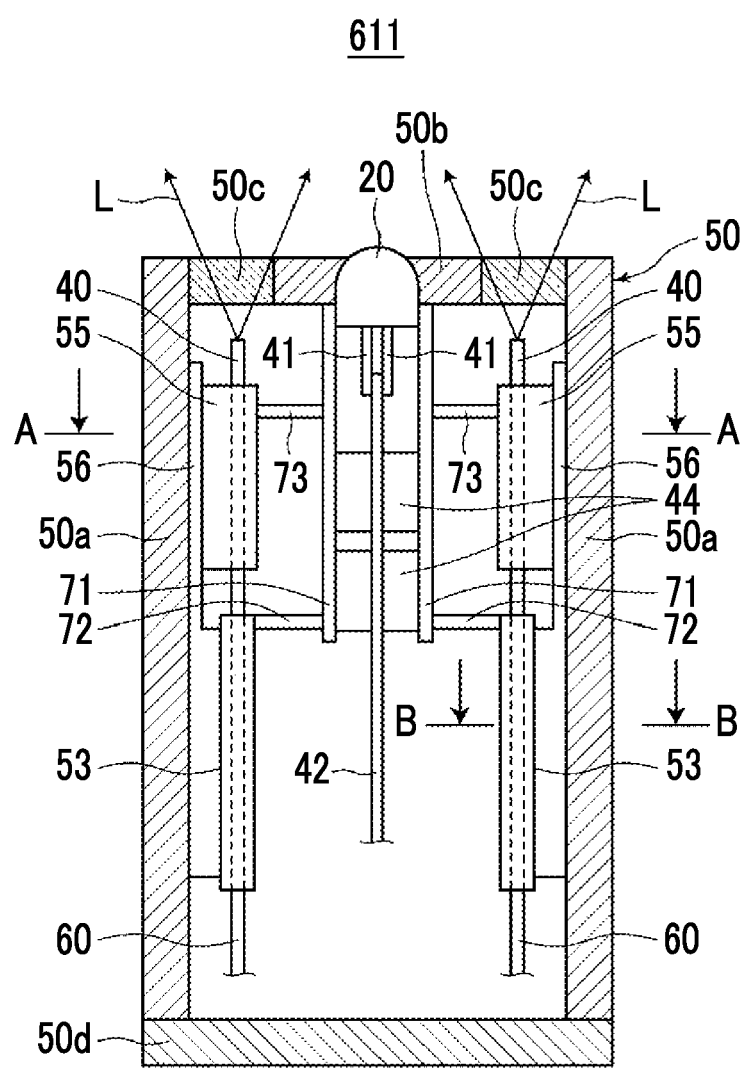
FIG. 10 is a side cross-sectional view showing a probe according to a sixth embodiment of the present invention.

Next, a probe 611 according to a sixth embodiment of the present invention will be described with reference to FIG. 10. FIG. 10 shows the side cross-sectional shape of the probe 611 of the present embodiment. The probe 611 is different from the probe 211 of the second embodiment shown in FIG. 6 in that a heat transfer plate 71 tightly fixed to the transducer array 20 and the preamplifier 44 and heat transfer plates 72 and 73 each having one end and the other end tightly fixed to the heat transfer plate 71 and the heat transfer member 53, respectively, are used instead of the heat transfer plate 51 and the heat transfer plate 52.

In the configuration described above, heat generated mainly from the preamplifier 44 and heat generated mainly from the transducer array 20 are satisfactorily transferred to the two side plates 50a through the heat transfer path of the heat transfer plate 71, the heat transfer plate 73, the fiber fixing member 55, and the frame member 56 and the heat transfer path of the heat transfer plate 71, the heat transfer plate 72, the heat transfer member 53, and the frame member 56. Therefore, heat can be satisfactorily dissipated from the two side plates 50a. As a result, also in the present embodiment, an excessive increase in the temperature of the top plate 50b of the housing 50 in contact with the subject M or the transducer array 20 and an excessive increase in the temperature of the vicinity thereof are prevented.

Seventh Embodiment

Figure 11:
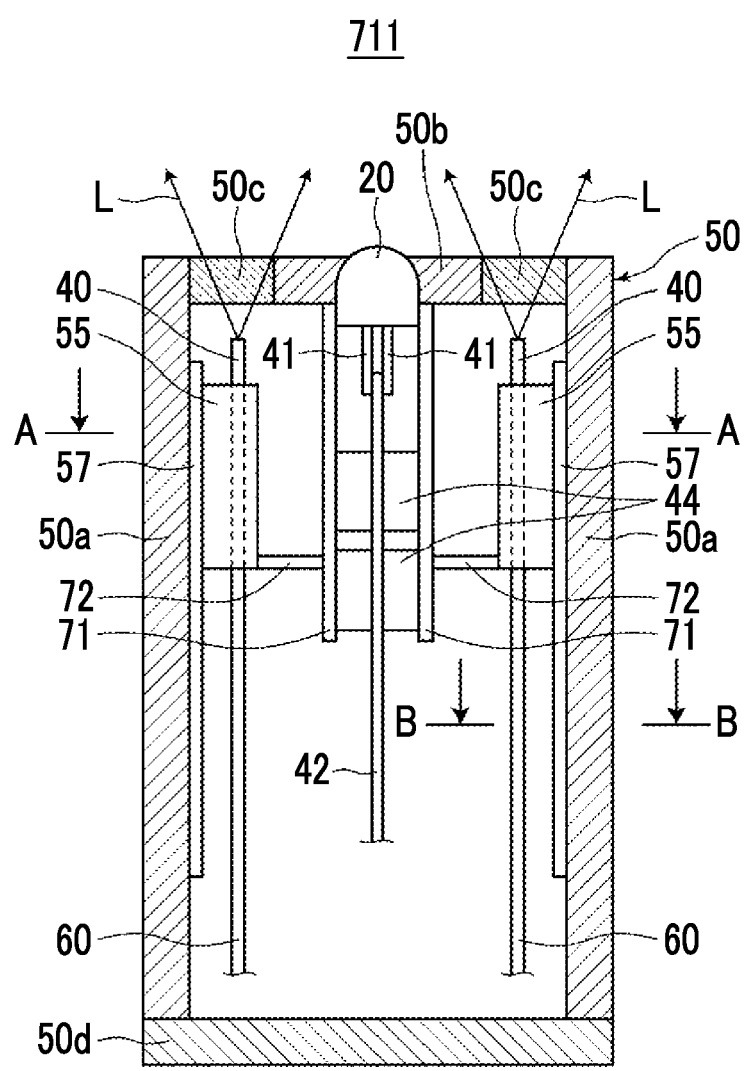
FIG. 11 is a side cross-sectional view showing a probe according to a seventh embodiment of the present invention.

Next, a probe 711 according to a seventh embodiment of the present invention will be described with reference to FIG. 11. FIG. 11 shows the side cross-sectional shape of the probe 711 of the present embodiment. The probe 711 is different from the probe 311 of the third embodiment shown in FIG. 7 in that a heat transfer plate 71 tightly fixed to the transducer array 20 and the preamplifier 44 and a heat transfer plate 72 having one end and the other end tightly fixed to the heat transfer plate 71 and the fiber fixing member 55, respectively, are used instead of the heat transfer plate 51 and the heat transfer plate 58.

In the configuration described above, heat generated mainly from the preamplifier 44 and heat generated mainly from the transducer array 20 are satisfactorily transferred to the two side plates 50a through the heat transfer path of the heat transfer plate 71, the heat transfer plate 72, the fiber fixing member 55, and the frame member 57. Therefore, heat can be satisfactorily dissipated from the two side plates 50a. As a result, also in the present embodiment, an excessive increase in the temperature of the top plate 50b of the housing 50 in contact with the subject M or the transducer array 20 and an excessive increase in the temperature of the vicinity thereof are prevented.

Eighth Embodiment

Figure 12:
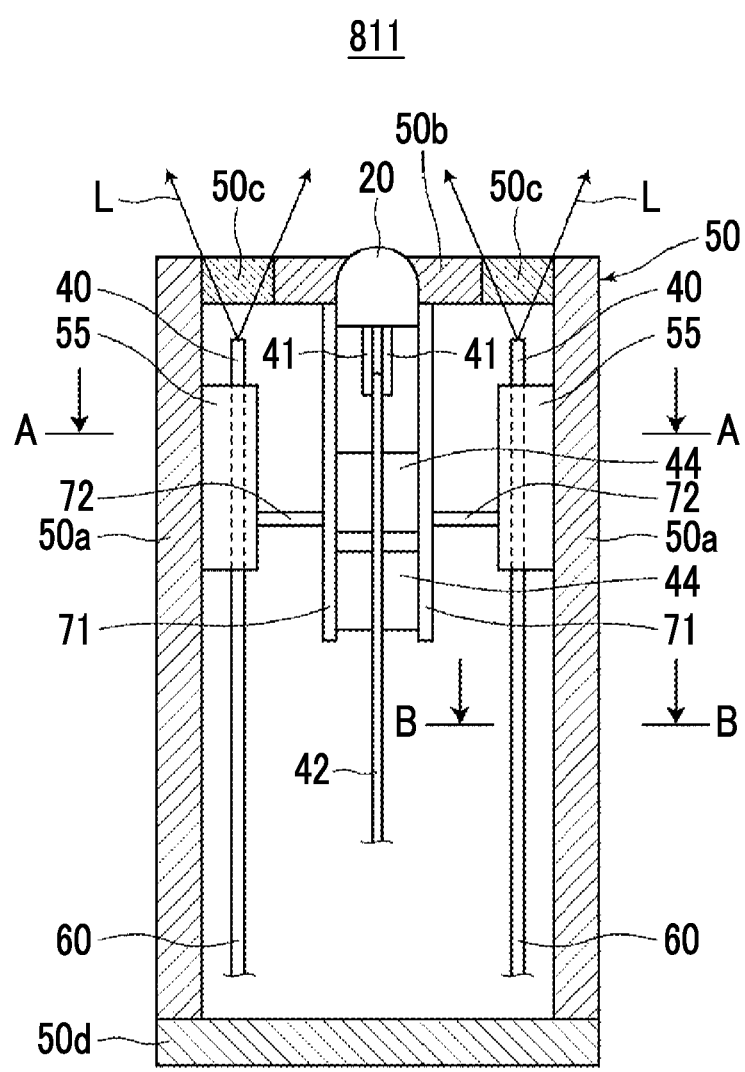
FIG. 12 is a side cross-sectional view showing a probe according to an eighth embodiment of the present invention.

Next, a probe 811 according to an eighth embodiment of the present invention will be described with reference to FIG. 12. FIG. 12 shows the side cross-sectional shape of the probe 811 of the present embodiment. The probe 811 is different from the probe 411 of the fourth embodiment shown in FIG. 8 in that a heat transfer plate 71 tightly fixed to the transducer array 20 and the preamplifier 44 and a heat transfer plate 72 having one end and the other end tightly fixed to the heat transfer plate 71 and the fiber fixing member 55, respectively, are used instead of the heat transfer plate 51 and the heat transfer plate 58.

In the configuration described above, heat generated mainly from the preamplifier 44 and heat generated mainly from the transducer array 20 are satisfactorily transferred to the two side plates 50a through the heat transfer path of the heat transfer plate 71, the heat transfer plate 72, and the fiber fixing member 55. Therefore, heat can be satisfactorily dissipated from the two side plates 50a. As a result, also in the present embodiment, an excessive increase in the temperature of the top plate 50b of the housing 50 in contact with the subject M or the transducer array 20 and an excessive increase in the temperature of the vicinity thereof are prevented.

In all of the probes of the embodiments described above, one light emitting unit 40 is disposed on each of both sides of the transducer array 20, which is an acoustic wave detector, with the transducer array 20 interposed therebetween. However, the present invention is not limited to such probes, and the present invention can also be applied to a probe in which a plurality of light emitting units are disposed on at least one of both sides of one acoustic wave detector, a probe in which only one acoustic wave detector and one light emitting unit are provided, or a probe in which a plurality of acoustic wave detectors are provided.

In the diagrams showing each embodiment described above, the housing 50 has been described as a quadrangular tubular shape having a constant cross-sectional shape over the entire length (length in the tube axis direction). However, the housing in the photoacoustic measurement probe of the present invention is not limited to such a quadrangular tubular shape. Even in a case where a part or the entirety of the housing 50 is formed in a quadrangular tubular shape, the housing 50 may be formed in various approximate quadrangular tubular shapes without being limited to a complete quadrangular tubular shape.

Figure 13:
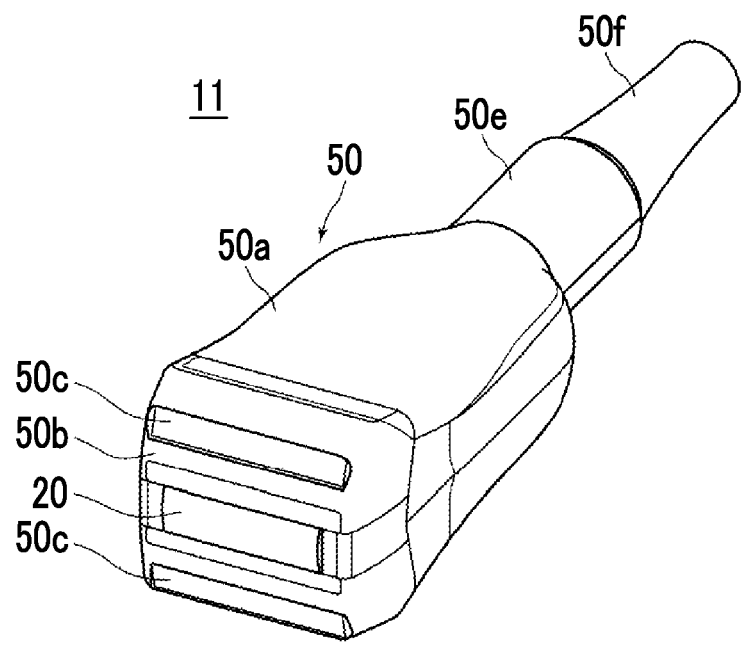
FIG. 13 is a perspective view showing a detailed shape example of a housing of a probe.
Figure 14:
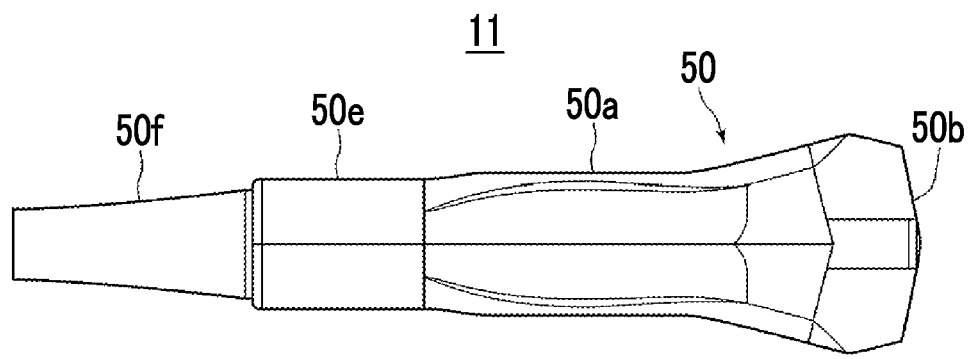
FIG. 14 is a side view of the probe shown in FIG. 13.

FIGS. 13 and 14 show examples of the shape of the housing 50 in detail. The following explanation will be continued on the assumption that this example of shape is applied to the probe 11 of the first embodiment. FIGS. 13 and 14 show the oblique shape and the side surface shape of the probe 11 of this example, respectively. As shown in these diagrams, the side plate 50a, which is formed in an approximate quadrangular tubular shape, of the housing 50 has a shape in which a quadrangular tubular portion on the distal end side having a relatively large cross section and connected to the top plate 50b and a quadrangular tubular portion, which is relatively long and has a relatively small cross section, are connected to each other in a tube axis direction. In using the probe 11, the above relatively long quadrangular tubular portion is gripped by the operator. A cylindrical base portion 50e is formed in the housing 50 continuously to this portion, and a sleeve 50f for allowing the wiring 42, the optical fiber 60, and the like shown in FIG. 2 to pass therethrough is provided continuously to the base portion 50e.

Figure 15:
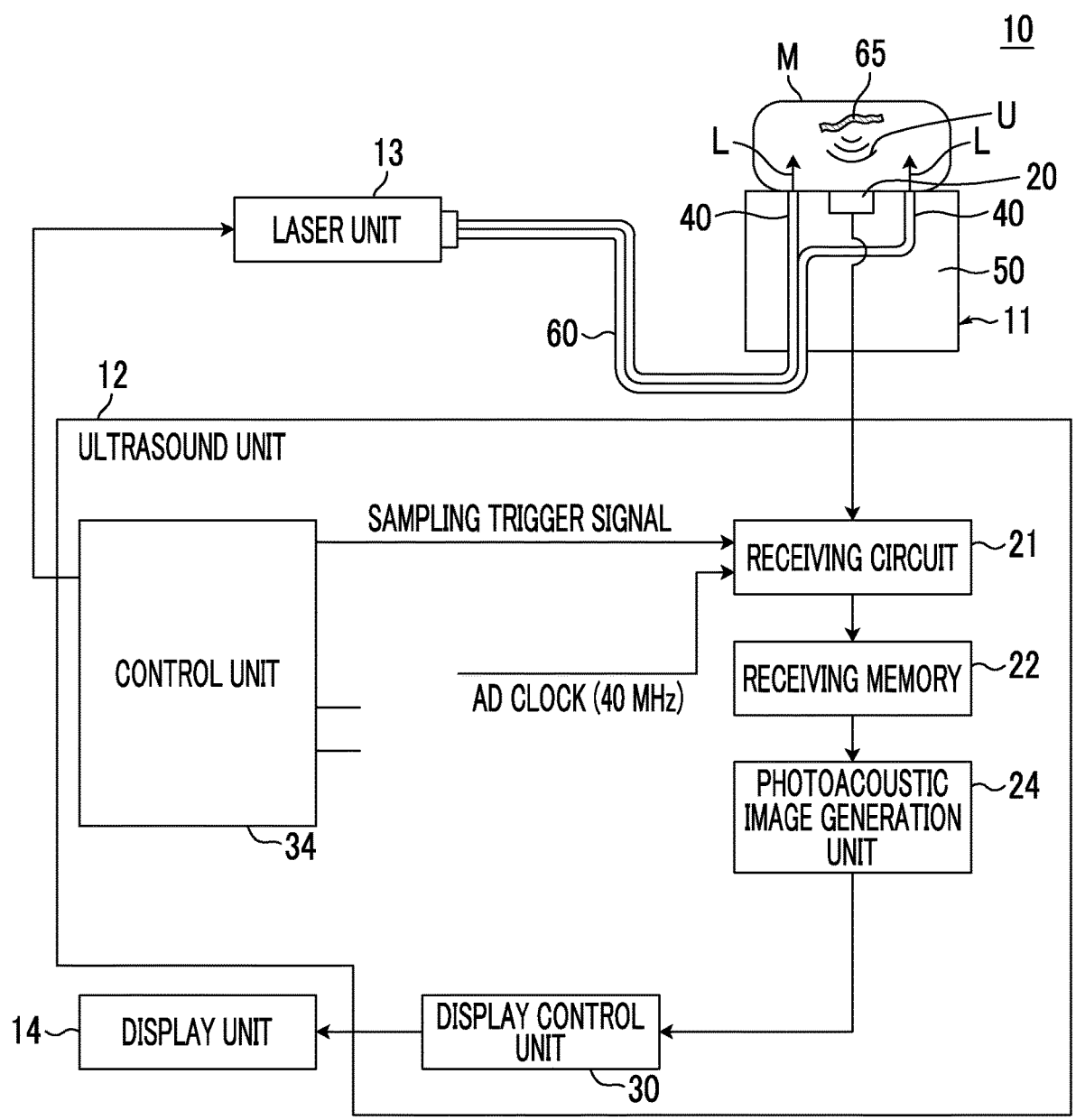
FIG. 15 is a schematic diagram showing the overall configuration of a photoacoustic measurement apparatus according to another embodiment of the present invention.

In addition, although the probe 11 applied to the photoacoustic measurement apparatus 10 capable of generating and displaying not only a photoacoustic image but also a reflected ultrasound image has been described, it is needless to say that the probe of the present invention can be applied to a photoacoustic measurement apparatus configured not to generate and display a reflected ultrasound image but only to generate and display a photoacoustic image. FIG. 15 shows an example of the photoacoustic measurement apparatus 10 configured as described above. The photoacoustic measurement apparatus 10 shown in FIG. 15 has a configuration in which the data separation unit 23, the ultrasound image generation unit 29, and the transmission control circuit 33 are removed compared with that shown in FIG. 1.

In addition, the photoacoustic measurement apparatus 10 described above is configured to generate and display a photoacoustic image. However, the probe of the present invention is not limited to such a photoacoustic measurement apparatus, and can be applied to all photoacoustic measurement apparatuses that perform certain measurement based on the detected photoacoustic wave. That is, in a case where the probe of the present invention is applied to the photoacoustic measurement apparatus, it is possible to prevent the probe surface in contact with the subject M and the vicinity thereof from excessively rising in temperature as described above.

EXPLANATION OF REFERENCES

10: photoacoustic measurement apparatus
11, 211, 311, 411, 511, 611, 711, 811: probe
12: ultrasound unit
13: laser unit
14: display unit
20: transducer array
21: receiving circuit
22: receiving memory
23: data separation unit
24: photoacoustic image generation unit
29: ultrasound image generation unit
30: display control unit
33: transmission control circuit
34: control unit
40: light emitting unit
43: fiber fixing member
44: preamplifier
50: housing
50a: side plate of housing
50b: top plate of housing
50d: bottom plate of housing
51, 52, 54, 58, 71, 72: heat transfer plate
53: heat transfer member
55: fiber fixing member
56, 57: frame member (holding member)
60: optical fiber
65: absorber
L: laser light (measurement light)

M: subject
U: acoustic wave

What is claimed is:

1. A photoacoustic measurement probe, comprising: a light emitting unit including a light guide plate that emits measurement light toward a subject; an optical fiber that guides the measurement light to the light emitting unit; an acoustic wave detector including a transducer array that detects an acoustic wave emitted from a part of the subject that has absorbed the measurement light and that includes a plurality of electroacoustic conversion elements arranged in at least a first direction; a preamplifier that amplifies an output of the acoustic wave detector; a housing including a tubular member having a quadrangular tubular shape and four side plates, the four side plates surrounding the tubular member, wherein the housing houses the light emitting unit, the optical fiber, the acoustic wave detector, and the preamplifier; a first heat conductive member including a heat transfer plate that is in direct contact with at least one of two side plates, an inner surface of each of the two side plates facing each other in the first direction, and the preamplifier to transfer heat generated by the preamplifier to the at least one side plate; and a second heat conductive member including a second heat transfer plate that is in direct contact with at least one of two side plates different from the at least one of two side plates with which the first heat conductive member is in contact and the side plate having the inner surface facing the inner surface of the side plate that is in contact with the first heat conducting member and the acoustic wave detector to transfer heat generated by the acoustic wave detector to the at least one of two side plates different from the at least one of two side plates with which the first heat conductive member is in contact and the side plate having the inner surface facing the inner surface of the side plate that is in contact with the first heat conducting member.

2. The photoacoustic measurement probe according to claim 1,
wherein a width of each of the two side plates with which the second heat conductive member is in contact is larger than a width of each of the two side plates with which the first heat conductive member is in contact.

3. The photoacoustic measurement probe according to claim 1,
wherein a plurality of the optical fibers extend in a tube axis direction of the tubular member and are arranged to be aligned in a direction parallel to the first direction, and the second heat conductive member has a portion disposed around the plurality of optical fibers.

4. The photoacoustic measurement probe according to claim 1, further comprising: a fiber fixing member including a plurality of grooves that fixes the plurality of optical fibers to the housing, wherein the second heat conductive member is in contact with at least one of two side plates different from the at least one of the two side plates with which the first heat conducting member is in contact on a proximal end side of at least one of two side plates different from the at least one of the two side plates with which the first heat conducting member rather than the fiber fixing member.

5. The photoacoustic measurement probe according to claim 1,
wherein the second heat conductive member also serves as a fiber fixing member including a plurality of grooves that fixes the plurality of optical fibers to the housing.

6. The photoacoustic measurement probe according to claim 1, wherein the second heat conductive member is in contact with an inner surface of at least one of two side plates different from the at least one of the two side plates with which the first heat conductive member through a holding member.

7. The photoacoustic measurement probe according to claim 1,
wherein two light emitting units are provided,
the acoustic wave detector is disposed on a distal end side of the tubular member, and
on the distal end side of the tubular member, the two light emitting units are disposed with the acoustic wave detector interposed therebetween in a second direction crossing the first direction.

8. A probe unit, comprising:
the photoacoustic measurement probe according to claim 1;
a light source that outputs measurement light; and
a connection unit that optically connects the measurement light to the light emitting unit of the photoacoustic measurement probe.

9. A photoacoustic measurement apparatus, comprising:
the photoacoustic measurement probe according to claim 1; and
a signal processing unit that generates a photoacoustic image based on a photoacoustic wave detection signal output from the photoacoustic measurement probe.

* * * * *